US006455050B1

(12) United States Patent
Ewasyshyn et al.

(10) Patent No.: US 6,455,050 B1
(45) **Date of Patent: *Sep. 24, 2002**

(54) PRODUCTION OF VIRUS AND PURFICATION OF VIRAL ENVELOPE PROTEINS FOR VACCINE USE

(75) Inventors: Mary Elizabeth Ewasyshyn, Willowdale (CA); Barry Ian Caplan, Don Mills (CA); Anne-Marie Bonneau, Longueil (CA); Michel Henri Klein, Willowdale (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 08/427,837

(22) Filed: Apr. 26, 1995

Related U.S. Application Data

(63) Continuation of application No. 07/773,949, filed as application No. PCT/CA90/00205 on Jun. 28, 1990, now Pat. No. 6,245,549.

(30) Foreign Application Priority Data

Jun. 29, 1989 (GB) .............................................. 8914968

(51) Int. Cl.[7] .............................................. A61K 39/155

(52) U.S. Cl. .............................. 424/211.1; 424/196.11; 424/199.1; 424/278.1; 435/235.1; 435/69.1; 530/350; 530/403

(58) Field of Search ......................... 424/196.11, 199.1, 424/202.1, 211.1; 435/5, 235.1, 69.1; 530/350, 403, 826

(56) References Cited

U.S. PATENT DOCUMENTS 5,284,764 A * 2/1994 Wathen .................. 435/240.2
5,288,630 A * 2/1994 Wathen .................. 435/240.2

OTHER PUBLICATIONS

Ray et al., Journal of Virology, vol. 62, No. 3, Mar. 1988. pp. 783–787.*

J. Gen. Virol., vol. 68, 1987, SGM, (GB), R. Ray et al.: "Glycoproteins of human parainfluenza virus type 3: affinity purification, antigenic characterization and reconstitution into lipid vesicles" pp. 409–418 see the whole article.

Biological Abstracts, vol. 78, 1984, (Philadelphia, PA, US), E.E. Walsh et al.: "Purification and characterization of GP90, one of the envelope glycoproteins of respiratory syncytial virus", see p. 5426, abstract 48223, & J. Gen. Virol. 65(4): 761–768, 1984.

Chemical Abstracts, vol. 111, No. 5, Jul. 31, 1989, (Columbus, Ohio, US), R.G. Arumugham et al.: "Interprotein disulfide bonding between F and G glycoproteins of human respiratory syncytial virus", see p. 235, abstract 35325x, Arch. Virol. 1989, 105 (1–2), 65–79.

Chemical Abstracts, vol. 107, No. 13, Sep. 28, 1987, (Columbus, Ohio, US), E.E. Walsh et al.: "Immunological differences between the envelope glycoproteins syncytial virus", see p. 485, abstract 113935e, & J. Gen. Virol. 1987, 68(8), 2169–78.

* cited by examiner

*Primary Examiner*—Laurie Scheiner
(74) *Attorney, Agent, or Firm*—Sim & McBurney

(57) ABSTRACT

Immunogenic envelope glycoproteins are produced from enveloped virus, such as of the paramyxoviridae family, particularly PIV-3 and RSV, by culturing the virus in the substantial absence of exogenous serum proteins, isolating the virus from the tissue culture, solubilizing the envelope glycoproteins and isolating the solubilized envelope glycoproteins by chromatography.

2 Claims, No Drawings

PRODUCTION OF VIRUS AND PURFICATION OF VIRAL ENVELOPE PROTEINS FOR VACCINE USE

This is a continuation of application Ser. No. 07/773,949 filed Jan. 25, 1991, now U.S. Pat. No. 6,245,549, which is a National Phase filing of PCT/CA90/00205 filed Jun. 28, 1990.

FIELD OF INVENTION

The present invention relates to the preparation and purification of envelope glycoproteins, particularly from the Paramyxoviridae family of human pathogenic viruses. The present invention also relates to the formulation of a mixture of the purified glycoproteins to give an efficacious and safe vaccine for use in infants and young children to protect against the diseases caused by the viruses.

BACKGROUND OF THE INVENTION

Human Parainfluenza type 3 (PIV-3) and Respiratory Syncytial subgroups A and B (RSV-A,B) viruses, which are members of the Paramyxoviridae, have been identified as major pathogens responsible for severe respiratory disease in infants and young children. It has been shown that both formaldehyde-inactivated and live-attenuated vaccines failed to provide adequate protection against these diseases in clinical trials. Currently, safe and effective vaccines for prevention against these viral infections are not available. Thus, the development of efficacious PIV-3 and RSV vaccines is urgently required.

The major immunogenic proteins of RSV and PIV-3 have been identified, thereby providing the scientific rationale for a sub-unit approach to vaccine development. It has been shown that an in vivo protective response is contingent on the induction of neutralizing antibodies against the major viral surface glycoproteins. For PIV-3, these protective immunogens are the HN protein, which has a M.W. of 72 kDa, and possesses both hemagglutinin and neuraminidase activities and the F (fusion) protein, which has a M.W. of 65 kDa, and is responsible for both fusion of the virus to the host cell membrane and cell-to-cell spread of the virus. Immunogenicity studies in hamsters have shown that antibodies to both HN and F proteins were essential for protection against challenge with PIV-3. In addition, the presence of antibodies to both envelope glycoproteins was reported to correlate with protection in children naturally infected with PIV-3. For RSV, the two immunogenic surface glycoproteins are the 80–90 kDa glycoprotein (G) and the 70 kDa fusion (F) protein. The G and F proteins are thought to be functionally analogous to the PIV-3 HN and F proteins, respectively. In humans, antibodies to both PIV-3 viral surface glycoproteins are necessary for protection against PIV-3 infection, whereas anti-fusion protein antibodies are sufficient to elicit a cross-protective response against RSV infection.

SUMMARY OF INVENTION

In accordance with the present invention, the inventors have found a process for the production and purification of both PIV-3 and RSV viruses as well as a procedure for the purification of viral envelope surface glycoproteins generally. This process results in preparations that are potent PIV-3 immunogens in experimental animals and may be acceptable for use as vaccines in children. This procedure also is directly applicable for the production of virus and the purification of surface glycoproteins from any of the enveloped viruses, such as influenza, in which the major envelope proteins are important in eliciting an immunogenic response. The invention also includes the highly-purified immunogenic glycoproteins.

DESCRIPTION OF INVENTION

In the present invention, enveloped viruses, such as PIV-3 and RSV viruses, are grown in tissue culture on cell substrates that are readily acceptable for use in human vaccine production, such as the human diploid cell line MRC-5, in a medium virtually free of exogenous serum proteins. Surprisingly, under these conditions the cells continue to produce PIV-3 for more than three weeks, entirely in the absence of exogenously added growth factors. This process enables multiple virus harvests of similar antigenic composition to be obtained from the same group of cells. The absence of exogenous serum proteins greatly facilitates the process of purification.

Viral supernatants are either filtered or spun at low speed to remove cellular debris and concentrated by ultrafiltration, when necessary. The virus then is pelleted by ultracentrifugation. The virus also can be isolated by passage of the ultrafiltration retentate over an affinity matrix, such as Cellufine sulfate. The viral envelope glycoproteins then are solubilized with an appropriate detergent (eg. Triton X-100 or octylglucoside). Insoluble viral nucleocapsids are removed from the solubilized material by centrifugation. We have shown that this step, while useful, need not be performed. The viral surface glycoproteins are purified from the glycoprotein enriched fraction by affinity chromatography. Possible affinity matrixes include lentil-lectin and concanavalin A covalently coupled to cross-linked Sepharose or cellulosic microporous membranes. Contaminating cellular and residual viral matrix proteins are eliminated in the flow-through and high salt washes. Viral surface glycoproteins then are eluted from the column in the presence of an appropriate competing sugar, such as methyl -D-mannopyranoside, in the presence or absence of salt. Highly purified glycoprotein preparations (as judged by Coomasie blue or silver stained SDS polyacrylamide gels) are obtained using this process.

In accordance with the present process, HN and F from PIV-3 and F and G proteins from RSV were affinity-purified. The PIV-3 HN and F proteins were found to be highly immunogenic when tested in three separate animal models, namely guinea pigs, hamsters and cotton rats. Immunization of animals with varying doses of HN and F elicited a strong anti-glycoprotein antibody response. When administered with the appropriate adjuvants such as Freund's or aluminum phosphate, the minimal immunoprotective dose can be significantly reduced. Thus the final vaccine preparation when formulated with aluminum phosphate as an adjuvant can be used as a readily injectable preparation for human use.

The effectiveness of the invention is not only limited to the preparation of the glycoproteins obtained from PIV-3 and RSV, but is applicable to coat proteins from all paramyxoviridae. Our invention also covers the use of similar methods of isolation and the use of adjuvants other than those mentioned.

EXAMPLES

Methods of determining hemagglutination (HA), tissue culture infectious dose$_{50}$ (TCID$_{50}$), hemagglutination inhibition (HAI), neutralization and anti-fusion titres not explicitly described in this disclosure are amply reported in the scientific literature and are well within the scope of those skilled in the art.

Example I

This Example illustrates the production of PIV-3 by a mammalian cell line.

A stock of human PIV-3 virus was used to infect MRC-5 cells grown on microcarrier beads in a Bellco flask. A 35-liter culture of confluent MRC-5 cells grown in medium containing 10% fetal bovine serum was drained and the MRC-5 cells washed 3 times with 15 liters each of medium CMRL 1969 containing 0.14% $NaHCO_3$. The cells were then infected with PIV-3 virus in a final volume of 10 liters of CMRL 1969 containing 0.14% $NaHCO_3$ and the virus allowed to adsorb to the cells for 2 hours at 37° C. with stirring. Following adsorption, an additional 25 liters of medium was added to the flask. These conditions reduced the serum proteins by an estimated 5,000 fold resulting in a final concentration of less than 0.002%. The cells were incubated at 37° C. for 5 days and the virus supernatant was collected. Approximately 35 liters of medium CMRL 1969 containing 0.2% $NaHCO_3$ was added to the cells and the culture was incubated for an additional 3 days and a second virus harvest obtained. An additional 35 liters of medium was then added and the cells incubated a further 4 days prior to final harvest. Aliquots of all three virus supernatants were assayed for infectivity and HA activity. Infectivity was determined in a standard $TCID_{50}$ assay using VERO cells, while HA activity was determined using guinea pig red blood cells at 37° C. The results, summarized in Table 1 below, clearly demonstrate that MRC-5 cells produce substantial amounts of virus when cultured in the relative absence of exogenous serum proteins and that the same group of MRC-5 cells are capable of providing three virus harvests each containing substantial levels of virus. The process was also successfully scaled up to 150L bioreactors.

Example II

This Example illustrates the preparation of purified PIV-3.

PIV-3 supernatant #2, obtained as detailed above, was processed using techniques readily amenable to large-scale vaccine production. The virus supernatant was first clarified by filtration. Tangential flow filtration with a Sartorius Sartocon Mini unit incorporating 0.3 $m^2$ of 0.45 um cellulose acetate membranes was used. Following clarification, virus was concentrated by tangential flow ultrafiltration using a Millipore Pellicon system incorporating 4 $ft^2$ of 100,000 nominal molecular weight cutoff PTHK membranes. The Pellicon retentate then was filtered through a 0.22 um Millipore Millipak 20 unit, and virus pelleted by ultracentrifugation at 100,000×g for 1 hour at 4° C. The purified virus was resuspended in buffer. The HA and infectivity results are presented in Table 2 below. Essentially complete recovery of HA activity and substantial recovery of virus infectivity was observed following processing. These results demonstrate the suitability of this process for PIV-3 purification.

Example III

This Example illustrates the purification of PIV-3 HN and F proteins by lentil-lectin or concanavalin A Sepharose-4B affinity chromatography.

Pelleted virus, at a protein concentration of 1.5 mg/mL was treated at room temperature for 1.5 hours with 2% v/v Triton X-100. Alternately, other detergents, such as octylglucoside or a combination of detergents (2% Triton X-100+2% w/v octylglucoside), can be used for protein extraction. When necessary, these preparations are subsequently dialyzed against 0.02% Triton X-100. The insoluble nucleocapsid cores then were removed by centrifugation at 15000×g for 1 hour at 4° C. HN and F proteins were purified from the glycoprotein-enriched supernatant by affinity chromatography on either a lentil-lectin or concanavalin A Sepharose column. The column first was washed with 10 bed volumes of PBS containing 0.02% v/v Triton X-100. Following sample loading, the column was washed with 10 volumes PBS containing 0.02% Triton X-100. This was followed by a high-salt wash consisting of 10 bed volumes of 0.35 M NaCl containing 0.02% v/v Triton X-100 in PBS. The HN and F proteins were eluted with 5 bed volumes of PBS containing 0.02% v/v Triton X-100 and 0.3 M methyl--D-mannopyranoside. The eluted surface glycoproteins were analyzed by SDS-PAGE and found to be ≧95% pure by Coomasie blue and silver staining of the polyacrylamide gels and scanning densitometry.

Example IV

This Example illustrates the purification of RSV F and G proteins by lentil-lectin or concanavalin A Sepharose-4B.

Pelleted RSV (Long strain), at a protein concentration of approximately 800 ug/mL, was treated at room temperature for 1.5 hours with 2% v/v Triton X-100. Insoluble nucleocapsid cores were removed by centrifugation at 15000×g for 1 hour at 4° C. F and G proteins were purified from the glycoprotein-enriched supernatant by affinity chromatography on either lentil-lectin or concanavalin A Sepharose column. The procedure used for protein purification was essentially identical to that used for purifying the PIV-3 HN and F proteins, as detailed in Example III.

The eluted surface glycoproteins were analyzed by SDS-PAGE and found to be >80% pure by silver staining of the polyacrylamide gels.

Example V

This Example illustrates the immunogenicity of the lentil-lectin purified PIV-3 glycoproteins in hamsters.

Four week old female hamsters (specific pathogen-free) were injected intramuscularly with either 1.0, 0.5 or 0.1 ug of lentil-lectin purified HN and F proteins, prepared as described in Example III, administered either alone or in combination with aluminum phosphate or Freund's adjuvants. Immediately after the 4 week bleed, animals were boosted with an equivalent dose of the antigen formulation. Sera samples also were taken 6 and 8 weeks after the primary injection. HAI, neutralizing and anti-fusion titres were determined (summarized in Table 3 below). Data from the first bleed, (taken 4 weeks after the primary dose) demonstrated that all HN and F formulations tested can elicit a primary immune response. Inclusion of either aluminum phosphate or Freund's adjuvants increased the HAI and neutralizing antibody responses approximately 10 and 30 fold, respectively. Animals responded in a dose-dependent manner to immunization with 1.0, 0.5 or 0.1 ug of adjuvanted antigen. Boosting the animals at 4 weeks with an equivalent dose of the antigen formulation resulted in a substantial increase in the HAI, neutralizing and anti-fusion titres. At the 1 ug dose of antigen, the immunopotentiating effects of both aluminum phosphate and Freund's adjuvants were evident. Thus, the immunogenicity of the lentil-lectin purified HN and F proteins has been clearly demonstrated. Antibody responses in guinea pigs and cotton rats were similar.

Example VI

This Example illustrates the immunogenicity of the concanavalin A purified PIV-3 glycoproteins in hamsters.

Hamsters (specific pathogen-free) were injected with either 1.0, 0.1, 0.05, or 0.01 ug of concanavalin purified HN and F proteins, prepared as described in Example III, in the presence of aluminum phosphate. Animals were immunized according to the schedule outlined in Example IV. Animals immunized with adjuvanted concanavalin A purified proteins (the results are summarized in Table 4 below) responded in a dose-dependent manner to primary injection with 1.0, 0.1, 0.05 or 0.01 ug of antigen. The minimal immunogenic dose of adjuvanted concanavalin A purified proteins was 0.01 ug. These results confirm the immunogenicity of the concanavalin A purified HN and F proteins.

Example VII

This Example illustrates the ability of the various HN and F formulations to elicit a protective response in immunized hamsters and cotton rats.

Hamsters immunized with either 1.0, 0.5, 0.1, or 0.01 ug of the lentil-lectin purified HN and F preparations, prepared as described in Example III, were challenged with live PIV-3 virus immediately after the 8 week bleed in order to evaluate the ability of the various HN and F formulations to confer protective immunity. Hamsters were sacrificed 3 days after challenge and their lungs removed and homogenized. Virus lung titres are summarized in Table 5 below. Control animals injected with diluted elution buffer supported the replication of $5.0 \log_{10} TCID_{50}$ units of virus per gram of lung tissue. In the absence of adjuvant, 75% of animals immunized with 1 ug of HN and F proteins had a detectable level of virus in their lungs. When HN and F was administered with either aluminum phosphate or Freund's adjuvant, two 0.1 ug doses of antigen protected all hamsters against live virus challenge. Virus was not detected in the lung homogenates. Similar results were obtained in cotton rats.

Concanavalin A-purified HN and F proteins were also able to elicit a protective response in immunized hamsters. Two 0.01 ug doses of Concanavalin A purified proteins, prepared as described in Example III, (combined with aluminum phosphate) protected 80% of the animals against live virus challenge. These results demonstrate the ability of both the lentil-lectin and concanavalin A-purified HN and F proteins to protect the lower respiratory tract of animals against live virus challenge.

The ability of the affinity-purified HN and F proteins to protect the upper respiratory tract of immunized animals against live virus challenge was also tested. Virus nasal wash titers are summarized in Table 6 below. The upper respiratory tract of animals immunized with two 1 ug doses of adjuvanted Concanavalin A purified proteins, prepared as described in Example III, was protected against PIV-3 infection. Virus was not detected in nasal washes from this group of animals. This was the only group of animals tested which showed significant protection in the upper respiratory tract following live virus challenge. Thus, concanavalin A-purified HN and F proteins, administered at a dose of 1 ug plus aluminum phosphate, can evoke an immunological response capable of protecting both the upper and lower respiratory tracts of hamsters against live virus challenge.

Example VIII

This Example illustrates that the various HN and F formulations do not cause "enhanced" histopathology in the lungs of immunized cotton rats following PIV-3 challenge.

Cotton rats were immunized with 1.0 or 0.1 ug of the lentil-lectin purified HN and F proteins, prepared as described in Example III, administered either alone or with aluminum phosphate. Animals were challenged intranasally with 100 median infectious doses of PIV-3 immediately after the 8 week bleed. Four days after virus challenge, cotton rats were sacrificed and lung sections were prepared for histopathological analysis. Lung sections from immunized and control animals were stained with hematoxylin and eosin, observed in a blinded fashion and evaluated for histopathology. The observed histopathological changes generally correlated with lung virus titers and varied conversely with HAI and neutralizing antibody levels. Animals immunized with placebo and then challenged with PIV-3 had the most notable histopathological changes. Sections of lung from these animals exhibited moderate to marked peribronchial and peribronchiolar lymphocytic infiltration interspersed with polymorphonuclear leukocytes and macrophages. Many of the bronchi and bronchioles observed were partially desquamified and the lumen of these passageways often contained a mixture of debris, leukocytes and serous exudate. Scattered microareas of interstitial pneumonitis and perivascular cuffing were occasionally seen. In contrast, pathological changes were minimal in animals immunized with protective doses of antigen. Most importantly, there was no evidence of enhanced pathology in lung sections of any group of immunized animals when examined four days after virus challenge. In no instance was the histopathology greater in immunized, challenged animals than in control animals immunized with placebo then challenged with PIV-3. It can, therefore, be concluded that the affinity-purified HN and F subunit vaccine has no short term immunopathological effects i.e.

TABLE 1

PI-3 Virus Production

| SAMPLE | VOLUME (ml) | HA ACTIVITY HAU† 0.5 ml | HA ACTIVITY Total | $TCID_{50}$ ACTIVITY Titer† ml | $TCID_{50}$ ACTIVITY Total |
|---|---|---|---|---|---|
| Supernatant #1 | 34,000 | 32 | $2.2 \times 10^7$ | $10^{6.0}$ | $5.4 \times 10^{10}$ |
| Supernatant #2 | 34,000 | 32 | $2.2 \times 10^7$ | $10^{7.0}$ | $3.4 \times 10^{11}$ |
| Supernatant #3 | 25,000 | 16 | $8.0 \times 10^6$ | $10^{6.2}$ | $4.0 \times 10^{10}$ |

TABLE 2

Purification of PI-3 Virus

| SAMPLE | HA ACTIVITY TOTAL UNITS | HA ACTIVITY % RECOVERY | $TCID_{50}$ ACTIVITY TOTAL | $TCID_{50}$ ACTIVITY % RECOVERY |
|---|---|---|---|---|
| Supernatant | $2.2 \times 10^7$ | 100 | $3.4 \times 10^{11}$ | 100 |
| Clarified | $2.2 \times 10^7$ | 100 | $2.1 \times 10^{11}$ | 62 |
| Retentate | $2.0 \times 10^7$ | 91 | $3.8 \times 10^{10}$ | 11 |
| Filtered retentate | $1.9 \times 10^7$ | 86 | $7.4 \times 10^{10}$ | 22 |
| 33k pellet | $2.5 \times 10^7$ | 114 | $4.8 \times 10^{10}$ | 14 |

TABLE 3

Serum Antibody Response of Hamsters Immunised with Various Lentil Lectin affinity-purified HN and F Formulations[a]

| Antigen Formulation | Dose | HAI[b] Primary 4 Week Bleed | HAI[b] Secondary 6 Week Bleed | HAI[b] Secondary 8 Week Bleed | Neutralisation[c] Primary 4 Week Bleed | Neutralisation[c] Secondary 6 Week Bleed | Neutralisation[c] Secondary 8 Week Bleed | Anti-Fusion[d] Primary 4 Week Bleed | Anti-Fusion[d] Secondary 6 Week Bleed | Anti-Fusion[d] Secondary 8 Week Bleed |
|---|---|---|---|---|---|---|---|---|---|---|
| Control | — | 10 | 10 | 10 | 10 | 10 | 10 | 4 | 4 | 4 |
| HN & F alone | 1.0 | 11 | 80 | 47 | 10 | 37 | 24 | 4 | 4 | 4 |
| HN & F + AlPO$_4$ | 1.0 | 100 | 640 | 640 | 79 | 645 | 457 | 8 | 16 | 8 |
|  | 0.5 | 50 | 645 | 457 | 56 | 513 | 457 | 4 | 8 | 8 |
|  | 0.1 | 28 | 575 | 575 | 28 | 407 | 407 | 4 | 8 | 4 |
| HN & F + Freund's | 1.0 | 380 | 1819 | 1819 | 380 | 2570 | 1513 | 8 | 32 | 8 |
|  | 0.5 | 134 | 2560 | 1621 | 1123 | 2560 | 2041 | 4 | 64 | 32 |
|  | 0.1 | 40 | 1071 | 758 | 28 | 912 | 912 | 4 | 64 | 32 |

[a] = Each value represents the reciprocal geometric mean titre from 6 animals
[b] = Serum dilution which inhibits erythrocyte agglutination by 4 hemagglutinating units of PIV-3
[c] = Serum dilution which blocks hemadsorption of 100 TCID$_{50}$ units of PIV-3
[d] = Serum dilution which blocks syncytia formation by 100 TCID$_{50}$ units of PIV-3

TABLE 4

Serum Antibody Response of Hamsters Immunised with Various Lentil Lectin affinity purified HN and F Formulations

| Antigen Formulation | Dose | HAI[b] Primary 4 Week Bleed | HAI[b] Secondary 6 Week Bleed | HAI[b] Secondary 8 Week Bleed | Neutralisation[c] Primary 4 Week Bleed | Neutralisation[c] Secondary 6 Week Bleed | Neutralisation[c] Secondary 8 Week Bleed |
|---|---|---|---|---|---|---|---|
| HN & F alone | 1.0 | 70 | 320 | 160 | 68 | 240 | 320 |
| HN & F + AlPO$_4$ | 1.0 | 320 | 960 | 960 | 293 | 1920 | 1280 |
|  | 0.1 | 50 | 480 | 240 | 55 | 480 | 480 |
|  | 0.05 | 30 | 267 | 200 | 25 | 373 | 200 |
|  | 0.01 | 35 | 256 | 224 | 28 | 288 | 176 |

[a] = Serum dilution which inhibits erythrocyte agglutination by 4 hemagglutination units of Para-3 virus.
[b] = Serum dilution which blocks hemadsorption of 100 TCID$_{50}$ units of Para-3 virus

TABLE 5

Response of Immunized Hamsters to PIV-3 Challenge[a] (Lower Respiratory Tract)

| HN & F Formulation | Dose of Antigen (ug) | % Animals With virus (b) | Mean Titre ± SEM log$_{10}$TCID$_{50}$ |
|---|---|---|---|
| Elution buffer |  | 100 | 4.9 |
| Lentil Lectin Purified |  |  |  |
| HN and F alone | 1.0 | 75 | ≤4.1 |
| HN and F + Aluminium phosphate | 1.0 | 0 | ≤1.9 |
|  | 0.5 | 0 | ≤1.9 |
|  | 0.1 | 0 | ≤1.9 |
| HN and F + Freund's | 1.0 | 0 | ≤1.9 |
|  | 0.5 | 0 | ≤1.9 |
|  | 0.1 | 0 | ≤1.9 |
| Concanavilin A Purified |  |  |  |
| HN and F alone | 1.0 | 0 | ≤1.9 |
| HN and F + Aluminium phosphate | 1.0 | 0 | ≤1.9 |
|  | .1 | 0 | ≤1.9 |
|  | .01 | 20 | 1.9 |

[a] = Animals were challenged with 10$^6$ TCID$_{50}$ units of PIV-3 and sacrificed 3 days later.
b = Minimum level of detectability was 10$^{1.9}$ TCID$_{50}$/g of lung tissue. Each value represents the mean value of 6 animals.

TABLE 6

Response of Immunized Hamsters to
PIV-3 Challenge[a] (Upper Respiratory Tract)

| HN & F Formulation | Dose of Antigen (ug) | % Animals With virus (b) | Mean Titre ± SEM $\log_{10}TCID_{50}$ |
|---|---|---|---|
| Elution buffer |  | 100 | 5.0 |
| *Lentil Lectin Purified* | | | |
| HN and F alone | 1.0 | 100 | 4.0 |
|  | 0.1 | 100 | 3.6 |
|  | 0.01 | 100 | 3.5 |
| HN and F + Aluminium phosphate | 0.1 | 100 | 4.2 |
|  | 0.01 | 100 | 4.2 |
| HN and F + Freund's | 0.1 | 100 | 2.4 |
|  | 0.01 | 100 | 4.7 |
| *Concanavilin A Purified* | | | |
| HN and F alone | 1.0 | 100 | 4.0 |
| HN and F + | 1.0 | 0 | ≦1.5 |
| Aluminium phosphate | .1 | 100 | 2.7 |
|  | .01 | 00 | 3.9 |

[a] = Animals were challenged with $10^6$ $TCID_{50}$ units of PIV-3 and sacrificed 3 days later.
[b] = Minimum level of detectability was $10^{1.9}$ $TCID_{50}$/ml of nasal wash. Each value represents the mean value of 6 animals.

SUMMARY OF DISCLOSURE

In summary of this disclosure, the present invention provides a novel procedure for preparing immunogenic envelope glycoproteins as well as the glycoproteins themselves. Modifications are possible within the scope of this invention.

What we claim is:

1. A composition for human administration comprising a protective, highly-immunogenic, non-immunopotentiating copurified mixture of HN and F glycoproteins of human parainfluenza type 3 prepared by copurification from native PIV-3 virus by affinity chromatography and an adjuvant containing alum (aluminum phosphate).

2. The composition of claim 1 formulated for administration by injection.

* * * * *